US009250224B2

(12) United States Patent
Byun (10) Patent No.: US 9,250,224 B2
(45) Date of Patent: Feb. 2, 2016

(54) TEST APPARATUS AND METHOD OF ACCELERATED PHOTO-DEGRADATION USING PLASMA LIGHT SOURCE

(71) Applicant: KOREA RESEARCH INSTITUTE OF CHEMICAL TECHNOLOGY, Daejeon (KR)

(72) Inventor: Doo Jin Byun, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 16 days.

(21) Appl. No.: 14/372,402

(22) PCT Filed: Jan. 16, 2013

(86) PCT No.: PCT/KR2013/000336
§ 371 (c)(1),
(2) Date: Jul. 15, 2014

(87) PCT Pub. No.: WO2013/109050
PCT Pub. Date: Jul. 25, 2013

(65) Prior Publication Data
US 2015/0017731 A1  Jan. 15, 2015

(30) Foreign Application Priority Data
Jan. 16, 2012  (KR) .................. 10-2012-0004690

(51) Int. Cl.
*G01N 17/00*  (2006.01)
*G01N 33/44*  (2006.01)

(52) U.S. Cl.
CPC .............. *G01N 33/442* (2013.01); *G01N 17/00* (2013.01); *G01N 17/004* (2013.01)

(58) Field of Classification Search
CPC ............................. G01N 17/00; G01N 17/02

USPC ........ 250/216, 221, 222.1, 252.1, 393, 461.1; 73/865.6
See application file for complete search history.

(56) References Cited

U.S. PATENT DOCUMENTS

| 5,226,318 A | 7/1993 | Huber et al. |
| 2002/0083782 A1 | 7/2002 | Suga |

(Continued)

FOREIGN PATENT DOCUMENTS

| JP | 2001-004526 A | 1/2001 |
| JP | 2006-322933 A | 11/2006 |

(Continued)

OTHER PUBLICATIONS

International Search Report mailed Mar. 11, 2013; PCT/KR2013/000336.

*Primary Examiner* — Kevin Pyo
(74) *Attorney, Agent, or Firm* — Ladas & Parry LLP (57) ABSTRACT

Disclosed is a test apparatus of accelerated photo-degradation measuring a degradation caused by photo-degradation in a material or a product by light containing UV light and visible light that simulate the solar light-inducing degradation. The apparatus includes a light irradiating unit configured to irradiate light using at least one electrodeless plasma lamp; a light condensing unit configured to collect light emitted from the light irradiating unit and irradiate the light uniformly into the surface of the specimen for the material or the product; and a specimen holder configured to fix the specimen, and the specimen holder being fixed at a predetermined position or rotated. Further, the at least one electrodeless plasma lamp generates light having a light power spectrum similar to a solar light in a region of UV light and short-wavelength visible light corresponding to a range of about 300-500 nm.

11 Claims, 5 Drawing Sheets

(56) References Cited

U.S. PATENT DOCUMENTS

| | | |
|---|---|---|
| 2005/0087768 A1 | 4/2005 | March et al. |
| 2006/0254372 A1 | 11/2006 | Scott et al. |
| 2007/0034026 A1 | 2/2007 | Maciver et al. |
| 2010/0005911 A1* | 1/2010 | Scott ............ G01N 21/25 73/865.6 |
| 2011/0079071 A1 | 4/2011 | Schultz et al. |

FOREIGN PATENT DOCUMENTS

| | | |
|---|---|---|
| JP | 2007-047169 A | 2/2007 |
| JP | 2008-216001 A | 9/2008 |

* cited by examiner

TEST APPARATUS AND METHOD OF ACCELERATED PHOTO-DEGRADATION USING PLASMA LIGHT SOURCE

TECHNICAL FIELD

The present invention relates to a technology for an accelerated photo-degradation test or a weathering test being capable of effectively performing a photo-degradation test by means of light including UV light and visible light simulating the solar photo-degradation, and more particularly, to a test apparatus and method for evaluating or predicting degradation and failure caused by the photo-degradation of a material and a product within a short-term period using the electrodeless plasma light source.

BACKGROUND ART

Typically, polymeric materials and organic materials used for forming plastics, rubbers, paint coatings, etc. are characterized by including macromolecules as a main component to which organic elements such as carbon, hydrogen, nitrogen, oxygen, etc. are covalently bonded, and have properties of relatively weak degradation by the degradation factor from light, heat, etc. compared to metal materials and ceramic materials. Physical degradation phenomenon such as creep, fatigue and stress relaxation is mostly based on destruction of bond between molecules or movement between molecules. On the contrary, chemical degradation by light such as UV is mostly companied with destruction of bond within molecules.

The degradation of the polymer by UV light is generated when the polymer absorbs the light energy corresponding to the energy destructing the main chain of the polymer. Here, the energy of destruction is called the bond dissociation energy.

The bond dissociation energy depends on a variety of molecule bond states from the weak bond energy such as a bond (O—O) of peroxide structure to the strong bond energy such as a bond (O—H) of hydroxyl group. In case of carbon-carbon bond or carbon-hydrogen bond constituting a main chain of molecule, the bond dissociation energy has a relatively high energy more than 83 kcal/mol.

Thus, a polymeric material consisting of only carbon-carbon bond or carbon-hydrogen bond such as polyethylene and polypropylene is expected to provide a relatively better light resistance. In fact, however, the light resistance may not be reached to the expectation. This result is estimated to be caused by a number of reasons. However, a problem of molecular structure due to carbon-carbon bond in the position of allyl located at an irregular defect structure or carbon-hydrogen bond of the tertiary carbon located at a chain structure such as vinyl and vinylidene structures formed by repeating irregular reaction or side reaction of monomer of polymerization may be issued to be a reason for a relatively lower dissociation energy. Accordingly, even in the polymer materials represented by the same molecular structure, light resistance may differ depending on kinds or amounts of such internal defects.

The difference of photo-degradation depending on the difference of the aforementioned molecular structure may occur even when molecular structures of a polymeric material or an organic material are different against the same light, but also is to be meant to occur even when conversely, light characteristics being applied to a polymeric material or an organic material having the same molecular structure are different. Thus, in the accelerated photo-degradation test or a weathering test, depending on how much the light characteristic used for the test apparatus is consistent with the actual solar light characteristic, it becomes the most important technical characteristics how much the photo-degradation phenomenon by the solar light outdoor can be reproduced or accurately predicted.

Radiant energy sending out from the sun to the surface of the earth contains a variety of light of wavelengths ranging from UV light, visible light and to infrared light. Such a division of the component of the solar light is merely separated to UV light, visible light and infrared light based on a specific wavelength band, and does not mean that such three types of different lights reach to the surface of the earth respectively. In fact, the solar light has a continuous spectrum over a wide wavelength band, and does not have any criteria to separate the solar light into such three kinds of lights.

The surface temperature of the sun is typically known to be 5,780 K, and light power spectrum of the solar radiation has a similar distribution of wavelength with a continuous spectrum of the blackbody also having a temperature of 5,780 K. However, the solar radiation is subject to reflection, scattering, absorption, etc. during passing through the earth's atmosphere. Therefore, the solar radiation energy passing through the earth's atmosphere is not consistent with the solar radiation energy reaching to the stratosphere outside the earth's atmosphere.

A wavelength band showing the most significant change is a short-wavelength UV light range of which most are filtered in the ozone layer in the earth. Therefore, UV light with a short-wavelength range of about 200-295 nm existing outside of the atmosphere is mostly removed, and the solar radiation energy reaching to the earth's surface contains light with a wavelength more than about 295 nm only.

Because of such characteristics, the amount of the short-wavelength UV light contained in the solar radiation energy is affected even by a way passing through the atmosphere, and also depending on an altitude of the sun from sea level and an altitude of the sun to the earth' surface, the effect on passing through the atmosphere appears differently.

When the solar radiation energy reaches to the earth's surface, as the light power spectrum of the solar light is affected by area and climate, the amount of UV light contained in the solar radiation and light power characteristics vary depending on area, season, weather and a time zone. For convenience sake, however, a certain reference is standardized for using. According to the Publication CIE 85-1989 which was established by International Commission on Illumination (CIE) as a reference for the standard light source for simulating the solar light for the test purpose, content ratio of UV light, visible light and infrared light in the solar radiation is typically 6.8%, 55.4% and 37.8%, respectively.

In the UV light contained in the solar radiation reaching to the earth' surface, content of the UV light with a short-wavelength of UVB region (about 280-315 nm) corresponding to the shortest wavelength is merely about 3%. However, as the light included in the UVB region has relatively strong light photon energy, even if the amount of the light in the UVB region is small, it can exert a strong effect on the photo-degradation of polymer and organic materials, thereby considering as an important artificial light source for the solar light simulation.

In order for the UV light exposed into an organic material such as a polymeric material to exert an effect on the chemical degradation, the energy of UV light exposed into the material must take place to be absorbed, which essentially depends on a unique UV light absorbing characteristic of the organic material. Such a characteristic is basically dependent on chemical molecular structure, and different absorbing characteristics are provided for each polymeric material. Typically, aspects of the UV absorption spectrum of many polymeric materials show trends that absorption rate at a short-wavelength region near 300 nm is increased and absorption rate at a long-wavelength region near 400 nm is decreased. As aspects are different for each polymeric material, however, it is difficult to generalize.

When a light source having a specific light power spectrum such as the solar light is irradiated to the polymeric material having different UV light absorption spectrum as above mentioned, the coupler of the polymeric material absorbs the light energy of the specific wavelength to make a chemical degradation to be progressed resulting in decomposition and oxidation reactions. Accordingly, an activated spectrum for the specific light source such as the solar light becomes to exist.

A variety of the activated spectrum caused by differentiated UV light absorption spectrum for each polymeric material consequentially becomes to a main reason causing an inconsistency between tests of photo-degradation by other light source with different light power spectrum in the UV light or the visible light region. This is the most fundamental reason causing an inconsistency between the test result with an artificial light source inconsistent with the light power spectrum of the solar light and the test result with the actual solar light. In particular, it is important whether in the UV light region exerting a direct effect on the photo-degradation, the light power spectrum between the solar light and the artificial light is inconsistent. Accordingly, in the photo-degradation test for the polymeric material and the organic material, it becomes the significance technically to select an artificial light source and also to use a filter with a function of removing UV light in a specific wavelength region.

However, there is no light source available having a light power spectrum fully consistent with the solar light in the developed artificial light sources so far. Even a xenon-arc lamp or a metal-halide lamp commonly employed for simulation for the solar light is not possible to provide a consistency with the solar light without using a filter, and even in case of using an appropriate filter, it is not possible to perfectly consist with the solar light power spectrum in the entire region as well as in the UV light region. Therefore, a realistic choice is taking a method to use a UV light filter capable of removing a short-wavelength UV light not contained in the solar light so as to consist with the solar light, even though the short-wavelength UV light severely is affected on the photo-degradation.

DISCLOSURE

Technical Problem

As described in the above, in the artificial light source by the prior art, it is in fact not possible to completely consist the light power spectrum of the artificial light source with the light power spectrum of the solar light in the entire UV light region. Accordingly, an investigation has been progressed to consist a short-wavelength UV light causing more intensive deteriorative action with the solar light.

In spite of the technical efforts, however, the artificial light source for simulating the solar light is still limited to a xenon-arc light source or a metal-halide global lamp, etc. Other high-pressure and low-pressure mercury lamp, a sunshine carbon-arc lamp, UV light fluorescent lamp, UV light LED lamp and some of the metal-halide lamps, etc. may emit light of UV light region. However, the whole light power spectrum differs from the solar light. Therefore, there is a still problem in those sources not suitable for a purpose of simulating the solar light.

Specifically, light sources which can be selected generally for the current simulation for the solar light are a xenon-arc source and a metal-halide global lamp. However, the photo-degradation test by those light sources has a still problem that the intensity of irradiation thereof is limited to a level similar to the intensity of irradiation of UV light of the solar light reaching to the earth's surface.

In other words, the solar light contains much visible light and infrared light in addition to the UV light which acts an important role to the photo-degradation of the polymeric material. Due to the strong heat collection effect being accompanied with the case of using higher level of intensity of irradiation with such a light source, the heat-sensitive polymeric material is subject to thermal degradation or thermal deformation by heat rather than by UV light. Because of this effect, in the typical accelerated photo-degradation test, the intensity of irradiation below 115 $W/m^2$ (in the range of about 300-400 nm) corresponding to three times of the light quantity based on average UV light in the daylight is used.

Because of such a problem, in the photo-degradation test using an artificial light source highly simulated to the solar light, it was not possible to perform an acceleration test of the highly-accelerated photo-degradation using a high intensity of UV light irradiation. In order to increase the intensity of UV light irradiation being exposed to the unit area, a variety of trials were attempted, for example, including that several light source lamps irradiating to the same point were installed with overlapping, and the distance between a specimen holder and the light source lamp was closest as much as allowed. However, such trials are merely tools for increasing the intensity of UV light irradiation irradiating from the light source, and does not provide a suitable method for preventing thermal degradation and thermal damage, thereby not being used normally.

On the contrary, some of the high and low pressure mercury lamps, metal-halide lamps have characteristics generating a very high level of intensity of UV light irradiation, even though contents of visible light and infrared light of those lamps are lower. Therefore, it is possible to perform a highly-accelerated test for irradiating a high intensity of UV light without giving thermal degradation or thermal damage to the polymeric material.

However, as the light power spectrums in the regions of UV light exerting an effect on the photo-degradation of the polymeric material and a short-wavelength visible light are greatly different from the spectrum of the solar light, the apparatus equipped with those lamps has a problem in not exactly reproducing a photo-degradation caused by the solar light. Due to such a problem, the apparatus is much limited in utilization and application of the result of the test. Typically, such a test apparatus equipped with those lamps is not used for predicting a photo-degradation caused by the solar light and rather is limited for an application of a simple comparative evaluation of UV light resistance.

Therefore, a test of photo-degradation for the products including organic materials including polymeric materials and organic materials may be progressed by two groups of lamps. One is a group of lamps of xenon-arc lamp and metal-halide lamp which have simulation characteristics to the solar light but are inadequate for a high intensity of UV light irradiation, and the other is a group of lamps of mercury lamp and metal lamp which are advantageous for a high intensity of UV light irradiation but are lacks of simulation characteristics to the solar light. Additionally, a UV light fluorescent lamp, a UV light-emitting diode lamp, etc. which are inadequate for a high intensity of UV light irradiation and also are lacks of simulation characteristics to the solar light are also used for light sources for the test of photo-degradation for the polymeric material.

The reason why such a variety of lamps are used for a test or a simulation for the photo-degradation of the polymeric material by the solar light is attributed to the fact that each lamp has various features and pros and cons. However, test apparatus of the photo-degradation having a characteristic of a high intensive UV light irradiation capable of using for a highly-accelerated photo-degradation apparatus suitable for a test of highly-accelerated photo-degradation together with a characteristic of light power suitable for a simulation to the solar light are very rare.

In this respect, the embodiments of the present invention provide complementary measures for both of problems of application of the above mentioned xenon-arc lamp and metal-Halide global lamp into the test apparatus for the highly-accelerated photo-degradation and of lacks of simulation characteristic to the solar light caused by the above mentioned high and low pressure mercury lamp, UV light fluorescent lamp and the like so that a highly-accelerated degradation test could be possible while maintaining a simulation characteristic for the photo-degradation by the solar light. Therefore, it is possible to evaluate or predict a degradation and a damage caused by the photo-degradation of a material and a product in a short-term period, using an electrodeless plasma lamp as a light source which is abundant with UV light and short-wavelength visible light, but contains little infrared light.

Using such an electrodeless plasma lamp of the present invention as a light source in the test apparatus of the photo-degradation, the embodiments of the present invention may provide an acceleration test apparatus of (highly-accelerated) photo-degradation capable of irradiating a light containing a high intensive UV light more than 180 W/m$^2$ which is difficult to attain with typical xenon-arc lamp and metal-halide global lamp.

Here, W/m$^2$ which is the unit of UV light irradiance represents an intensity of irradiation of UV light in the range of about 300-400 nm.

Further, the embodiments of the invention may provide a test apparatus and method of the accelerated photo-degradation using an electrodeless plasma light source that makes it possible to predict and evaluate in a short-term period characteristics of photo-degradation caused by light such as UV light or visible light, etc. in polymeric materials and organic materials, organic-inorganic composite materials such as plastic, rubber, paint, coating, adhesive, oil, paper or the like, or components and products containing such materials.

Further, the embodiments of the invention may provide a test apparatus and method of the accelerated photo-degradation using an electrodeless plasma light source that makes it possible to perform an acceleration test of highly-accelerated photo-degradation while minimizing thermal degradation or thermal damage thanks to the fact that the light source is abundant with UV light and visible light, but contains little infrared light.

Further, the embodiments of the invention may provide a test apparatus and method of the accelerated photo-degradation using an electrodeless plasma light source that makes it possible to evaluate or predict a degradation and a damage caused by the photo-degradation of a material and a product in a short-term period, using an electrodeless plasma lamp as a light source which is abundant with UV light and short-wavelength visible light, but of which ratio of infrared light is low.

Technical Solution

In accordance with an embodiment of the present invention, there is provided a test apparatus of accelerated photo-degradation using an electrodeless plasma lamp as a light source. The test apparatus may include a light irradiating unit configured to irradiate light using at least one electrodeless plasma lamp; a light condensing unit configured to collect light emitted from the light irradiating unit and irradiate the light uniformly into the surface of the specimen for the material or the product; and a specimen holder configured to fix the specimen, wherein the specimen holder being fixed at a predetermined position or rotated.

Further, The test apparatus may further comprise a plurality of light pipes connected to a plurality of electrodeless plasma lamps and configured to irradiate the light to a specimen chamber where the specimen holder is located, wherein each light pipe being in a shape of pipe including a material having a reflectivity of the UV light more than about 90% to the inside of the pipe; a specimen chamber partition wall including the specimen chamber, wherein each of the light pipes is inserted vertically into each side of the partition wall with a shape of polygon or circle, and the partition wall is arranged to irradiate light from the plurality of light-emitting lamps to the side of the specimen holder; a water spray nozzle configured to spray water to the specimen, wherein the water being sprayed from the exterior of the specimen holder; and an air conditioning unit configured to adjust temperature and humidity of the specimen chamber.

Further, the light pipe may be finished with a quartz glass plate coated with an anti-fogging agent or a water-repellent coating on the cross section or both sides inserted into the specimen chamber.

Further, the test apparatus may further comprise an immersing unit configured to move or fall the specimen holder into a water tank filled with water and to immerse the specimen in the ultrasonic vibration water tank for a predetermined period.

In accordance with another embodiment of the present invention, there is provided a test apparatus of accelerated photo-degradation using an electrodeless plasma light source. The apparatus may comprise a user interface configured to receive a control command; a control unit configured to perform the test of accelerated photo-degradation based on the control command and to perform a measurement for an intensity of UV light irradiating to the surface of the specimen in a certain wavelength or a band of the wavelength range; a light irradiating unit configured to irradiate light containing UV light and visible light simulating the solar light-inducing degradation using at least one electrodeless plasma light source under the control of the control unit; and a specimen holder configured to fix the specimen, wherein the specimen holder being fixed at a predetermined position or being rotated so as for the light to irradiate uniformly to the specimen under the control of the control unit.

Further, the light irradiating unit may comprise light-transmitting rods connected to a plurality of electrodeless plasma lamps and configured to transmit the light to the specimen chamber where the specimen holder is located, each of the light-transmitting rods having a shape of a light pipe or rod vertically inserted into each segment of a specimen chamber partition wall with a shape of polygon or circle.

Further, the control unit may be configured to control an air conditioning unit adjusting temperature and humidity of the specimen chamber and to receive UV light irradiation quantity from a UV light radiometer measuring a UV light irradiation quantity periodically or continuously to control the light irradiating unit so as for a constant intensity UV irradiance to maintain.

Further, the test apparatus may further comprise an immersing unit configured to move or fall the specimen holder into a water tank filled with water and to immerse the specimen in the ultrasonic vibration water tank for a predetermined period under the control by the control unit.

In accordance with an embodiment of the present invention, there is provided a test method of accelerated light-inducing degradation using an electrodeless plasma light source. The method may comprise receiving, at a control unit of a test apparatus of accelerated light-inducing degradation, a control command from a user interface; irradiating, based on the control command, light containing UV light and visible light simulating the solar light-inducing degradation to a specimen using at least one electrodeless plasma lamp; fixing a specimen holder with a specimen at a predetermined position within a specimen chamber or rotating; and identifying temperature, humidity and UV light irradiation quantity of the specimen chamber and adjusting the identified to a preset reference.

Further, the irradiating light to a specimen may comprise collecting the light emitted from the at least one electrodeless plasma lamp at a light condensing unit and irradiating the collected light to the surface of the specimen. Further, the at least one electrodeless plasma lamp has light power that comes to be higher gradually as wavelength becomes longer up to about 300 nm to 500 nm and that comes to be lower gradually as wavelength becomes in the region of about 600 nm to 750 nm to generate light having a light power spectrum similar to the solar light, and an intensity of infrared light region is lower than the intensity of the solar light or xenon-arc light source.

Advantageous Effects

The test apparatus and method of the accelerated photo-degradation using the electrodeless plasma light source according to the above-described embodiments of the present invention has one or more effects as described below.

According to the test apparatus and method of the accelerated photo-degradation using the electrodeless plasma light source according to the embodiments of the present invention, with the utilization of the electrodeless plasma lamp, there may be provided a test method of the highly-accelerated photo-degradation with a high intensity of UV light irradiation which is difficult to implement with the conventional xenon-arc lamp or the like. As the electrodeless plasma lamp has a similar light power distribution as the solar light in UV light and short-wavelength visible light region, differentially the prior art UV light-emitting lamp such as an open flame carbon-arc lamp or a metal ring lamp, there may be provided a accelerated acceleration test method capable of simulating more accurately the solar photo-degradation.

Further, as the electrodeless plasma lamp of the embodiments of the present invention has less content of infrared light than the xenon-arc lamp, it may be possible to effectively suppress heat collection effect being accompanied as an intensity of UV light irradiation goes higher in order to improve characteristic of promotion. Therefore, it may be provided a convenient tool in controlling a temperature of specimen so as for more accurate photo-degradation mechanism to be reproduced.

Also, in the embodiments of the present invention, a method of immersing the specimen into the ultrasonic water tank which is necessary for materials requiring an effect of moisture infringement in the acceleration test of the photo-degradation may be provided. Therefore, it may be used as a method for improving field reproducibility in the acceleration test of the photo-degradation of polymeric materials and products being influenced for a durability of photo-degradation by means of additives such as an antioxidant agent or light stabilizing agent.

In addition, as the electrodeless plasma lamp of the embodiments of the present invention has a much longer life time than the open flame carbon-arc lamp as well as the common xenon-arc lamp and metal ring lamp, it may avoid a problem of lacks of test reproducibility caused by a frequent lamp replacement during the test, and also a cost burden of operating a system can be reduced so much. In general, life time of a xenon-arc lamp and a metal ring lamp is 1,500 hours. On the contrary, life time of the electrodeless plasma lamp is a minimum 5,000 hours and generally more than 10,000 hours, which makes a reliable operation of the system possible. Such a characteristic of the electrodeless plasma lamp provides an advantage when a test of long-term period photo-degradation under the condition of acceleration test using a high intensity of UV light irradiation is performed.

As described in the above, a test method of the accelerated photo-degradation using the electrodeless plasma light source according to the embodiments of the present invention provides the effects of a shortened period of product development as well as a reduced cost of development. Also, thanks to an accurate reproducibility of the mechanism of field degradation and failure, an accurate acceleration test method for improving a quality of product and a life time is provided.

BEST MODE

The advantages and features of exemplary embodiments of the present invention and methods of accomplishing them will be clearly understood from the following description of the embodiments taken in conjunction with the accompanying drawings. However, the present invention is not limited to those embodiments and may be implemented in various forms. It should be noted that the embodiments are provided to make a full disclosure and also to allow those skilled in the art to know the full scope of the present invention. Therefore, the present invention will be defined only by the scope of the appended claims. Similar reference numerals refer to the same or similar elements throughout the drawings.

In the following description, well-known functions or constitutions will not be described in detail if they would obscure the invention in unnecessary detail. Further, the terminologies to be described below are defined in consideration of functions in the invention and may vary depending on a user's or operator's intention or practice. Accordingly, the definition may be made on a basis of the content throughout the specification.

The combinations of each step in respective blocks of block diagrams and a sequence diagram attached herein may be carried out by computer program instructions. Since the computer program instructions may be loaded in processors of a general purpose computer, a special purpose computer, or other programmable data processing apparatus, the instructions, carried out by the processor of the computer or other programmable data processing apparatus, create devices for performing functions described in the respective blocks of the block diagrams or in the respective steps of the sequence diagram. Since the computer program instructions, in order to implement functions in specific manner, may be stored in a memory useable or readable by a computer aiming for a computer or other programmable data processing apparatus, the instruction stored in the memory useable or readable by a computer may produce manufacturing items including an instruction device for performing functions described in the respective blocks of the block diagrams and in the respective steps of the sequence diagram. Since the computer program instructions may be loaded in a computer or other programmable data processing apparatus, instructions, a series of processing steps of which is executed in a computer or other programmable data processing apparatus to create processes executed by a computer to operate a computer or other programmable data processing apparatus, may provide steps for executing functions described in the respective blocks of the block diagrams and the respective sequences of the sequence diagram.

Moreover, the respective blocks or the respective sequences may indicate modules, segments, or some of codes including at least one executable instruction for executing a specific logical function(s). In several alternative embodiments, it is noticed that functions described in the blocks or the sequences may run out of order. For example, two successive blocks and sequences may be substantially executed simultaneously or often in reverse order according to corresponding functions.

Hereinafter, the embodiments of the present invention will be described in detail with reference to the accompanying drawings.

Figure 1:
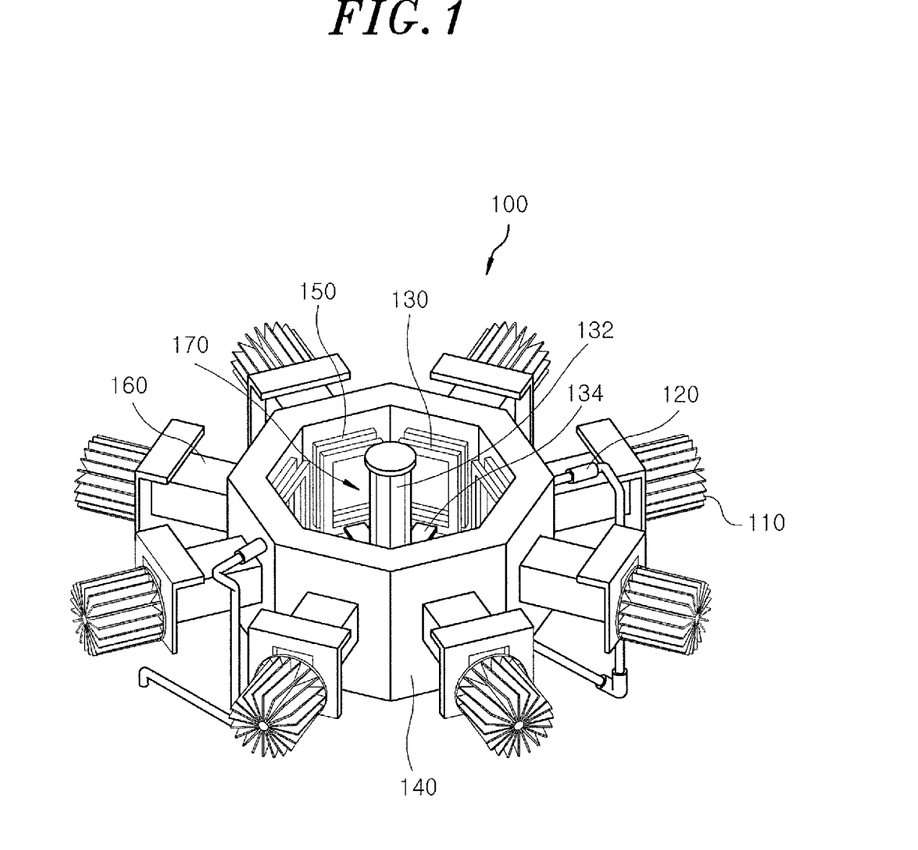
FIG. 1 and FIG. 2 are structural views illustrating a structure of a test apparatus of accelerated photo-degradation using an electrodeless plasma light source, according to an embodiment of the present invention, wherein FIG. 1 includes a number of electrodeless plasma light sources that are arranged horizontally in a circle, and FIG. 2 includes a number of electrodeless plasma light sources that are arranged vertically.

FIG. 1 is a structural view illustrating a structure of a test apparatus of accelerated photo-degradation using an electrodeless plasma light source, according to an embodiment of the present invention, wherein a number of electrodeless plasma light sources are arranged horizontally in a circle.

Referring to FIG. 1, a test apparatus 100 of the accelerated photo-degradation may include an electrodeless plasma source 110, a water spray nozzle 120, a specimen holder 130, a specimen chamber partition wall 140, a quartz glass plate 150, a light pipe 160, and a specimen chamber 170.

The light pipe 160 connected to the electrodeless plasma source 110 is referred as a light irradiating unit. The light pipe 160 is made of aluminum sheet with a size of 6 cm in width, 6 cm in height and 18 cm in length for reflecting UV light, and may be employed by eight in accordance with the number of the light sources.

The electrodeless plasma light sources 110 and the light pipes 160 may be connected correspondingly one by one to be arranged in a shape of octagon. The specimen chamber partition wall 140 which is an octagonal shape may include the specimen chamber 170 in the center. The specimen chamber partition wall 140 to be manufactured with a predetermined thickness may be composed to a structure with the light pipe 160 inserted vertically at each side. In this case, the specimen chamber partition wall 140 may be composed to other shape than the octagonal shape depending on the implementation method.

The electrodeless plasma source 110 may be located outside of the octagonal shape, and the end of the light pipe 160 may be connected into the ring of the regular octagon shape without a gap. The octagonal shaped light pipe 160 may be configured with the exit to be blocked by the quartz glass plate 150 coated with an antifogging agent. With this configuration, the light irradiating from the light pipe 160 may be irradiated to the specimen chamber 170 in a circular shape. In the light pipe 160 with a length of 18 cm, the length up to 7 cm is extruded from the wall surface of stainless steel separating the specimen chamber into the inner chamber and the outer chamber and is located at the inner chamber of the specimen chamber, and the remaining length of 11 cm is located at the machine room in the outer chamber of the specimen chamber.

The plastic specimen which is injected to a rectangular shape with a size of 47 mm in width, 67 mm in height and 3 mm in thickness may be fixed to the specimen holder 130 where total eight specimens are placed vertically on the octagonal shaped holder. The octagonal shaped specimen holder 130 may be located so as to substantially abut on the exit of the octagonal shaped light pipe 160, i.e. on the quartz glass plate 150 so that the specimen holder 130 can be formed in a rotatable holder rotating at a constant speed of 1-10 rpm. In this regard, when the specimen holder 130 is rotated, the holder 130 may be arranged in a circle so that the light can be irradiated from the light-emitting source 110 into the direction of the inside of the circle.

That is, the rotatable holder is configured to have a hub structure with a handle of the specimen holder or a column 132 as a rotating axis. The bottom of the handle of the specimen holder or the column 132 is provided with a radial structure or a specimen holder bushing 134 to which the bottom of the specimen holder 130 can be connected. With this configuration, each of the specimen holders 130 connected to the radial specimen holder bushing 134 can be rotated at the same time as the handle of the specimen holder 130 or the column 132 rotates.

In the surroundings of the specimen holder 130, the water spray nozzle 120 for spraying water to the position to be exposed to the irradiating light and a compressed air injection nozzle may be mounted. The specimen holder 130 may be equipped with an air pressurized moving unit in order to move up and down. During the time of irradiating, the specimen holder 130 may move up and be located at the position to be exposed by the focused light, and during the time of immersing into the water tank filled with water, the specimen holder 130 may move down and be located at the immersing position.

Such a movement of the specimen holder 130 is automatically controlled so as to be positioned for the given time by an operating program of a control unit 300. In the water tank at the bottom where the immersion test is in progress, a unit of temperature control function and a unit of ultrasonic vibration function are mounted to allow an ultrasonic vibration test with a desired temperature to be performed during the time of immersion.

A specimen chamber where the specimen holder 130 is located is designed to be controlled for the temperature and the humidity through an air conditioning unit, and also may be equipped with a T-type fluorine resin-based wired temperature sensor in order to directly measure a temperature of the surface of the specimen. In addition, a UV light radiometer may be mounted so as to be positioned at the same plane as the surface of the specimen in order to measure a UV light irradiation quantity irradiating to the surface of the specimen.

Meanwhile, the light irradiating unit may be configured in a different manner. For example, a light irradiating unit including an electrodeless plasma light source, a liquid light guide and a rod-like equalized condensing unit 161 shown in FIG. 2 (e.g., a light-transmitting square rod of a quartz glass material) may be used. The condensing unit 161 of the light irradiating unit may be fixed to the exact center of the plastic specimen injected with a rectangular shape with a size of 47 mm in width, 67 mm in height and 3 mm in thickness, and a lens of the condensing unit may be focused so as for an image of light to be well formed at 7 cm distance from the surface of the specimen.

Figure 3:
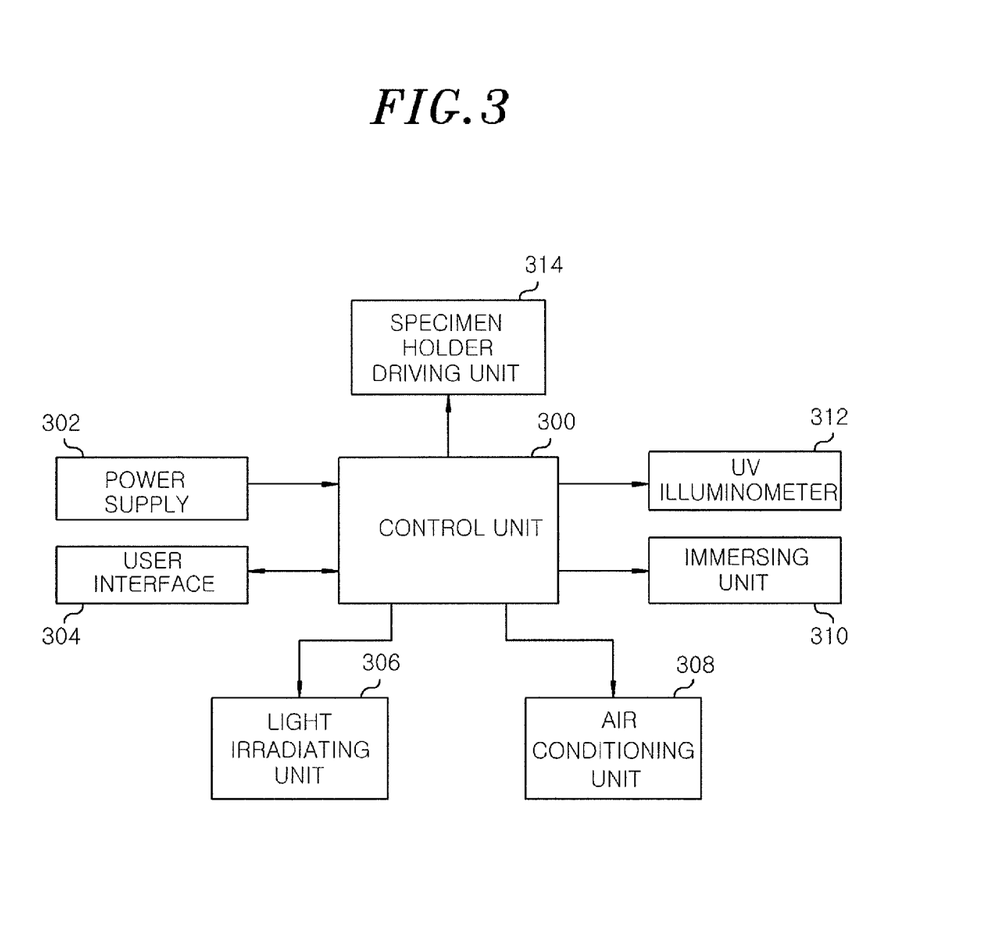
FIG. 3 is a block diagram illustrating a structure of a test apparatus of a accelerated photo-degradation using an electrodeless plasma light source, according to an embodiment of the present invention.

FIG. 3 is a block diagram illustrating a structure of a test apparatus of a accelerated photo-degradation using an electrodeless plasma light source, according to an embodiment of the present invention.

Referring to FIG. 3, the test apparatus 100 of the accelerated photo-degradation may include a control unit 300, a power supply 302, a user interface 304, a light irradiating unit 306, an air conditioning unit 308, an immersing unit 310, a UV light radiometer 312, and a specimen holder driving unit 314.

Specifically, the power supply 302 may provide an electrical power to each of the functional blocks within the test apparatus 100 of the accelerated photo-degradation. The user interface 304 may be interlocked with a user driving the test apparatus 100 of the accelerated photo-degradation via wired or wireless network, and may receive a control command via a user terminal or the like and to transmit the input control command to the control unit.

The control unit 300 may control each of the functional blocks and may include an operation program for driving the test apparatus 100 of the accelerated photo-degradation. The operation program is prepared for performing the test of the accelerated photo-degradation, and may control the light irradiating unit 306, the air conditioning unit 308, the immersing unit 310, the UV light radiometer 312, the specimen holder driving unit 314, etc.

First, the control unit 300 may control the light irradiating unit 306 including the electrodeless plasma light source 110 to emit so as for the light to be irradiated to the specimen. The air conditioning unit 308 may include a temperature control unit and a humidity control unit installed in the specimen chamber. The air conditioning unit 308 may transmit the measured temperature and humidity to the control unit periodically, thereby controlling temperature and humidity under the control by the control unit 300.

There are several methods for controlling temperature and humidity. For example, one method is to utilize a forced air blowing or a water spraying to the specimen using a circulation type cooling device, and another method is to utilize a cooled air blowing to the specimen using a chiller or a heat exchanger etc. within the circulation type cooling device which cools the air inhaled from the outside of the chamber.

Such control methods may be performed under the control by the control unit 300, after interlocking the test apparatus 100 of the accelerated photo-degradation and the circulation type cooling device.

The immersing unit 310 may bring the specimen holder 130 down to the water tank filled with water. The UV light radiometer 312 may measure periodically or continuously the irradiation quantity of the UV light to be irradiated to the surface of the specimen and transmit the measured value to the control unit 300.

The UV light radiometer 312 may perform a checking the irradiation quantity, for example, at the time between the initiating time and the finishing time of each test of the photo-degradation for the intensity of irradiation of the UV light, and transmit the calibration to the control unit 300. In this respect, the control unit 300 may then control a constant intensity of irradiance of the UV light so as to be maintained during the test of the photo-degradation by application of the average value of the intensity of irradiance of the UV light or via an automatic controlling by the light irradiating unit 306 using a feedback.

The specimen holder driving unit 314 may rotate the specimen holder 130 at a constant speed under the control by the control unit 300, or may move up and down the specimen holder 130 via controlling an air pressure. In other words, during the immersion test, the specimen holder driving unit 314 under the state of interlocking with the immersing unit 310 may move down the specimen holder so as for the specimen to be immersed.

Such an operation method of the test apparatus 100 of the accelerated photo-degradation will be described in detail with reference to FIG. 4.

Figure 4:
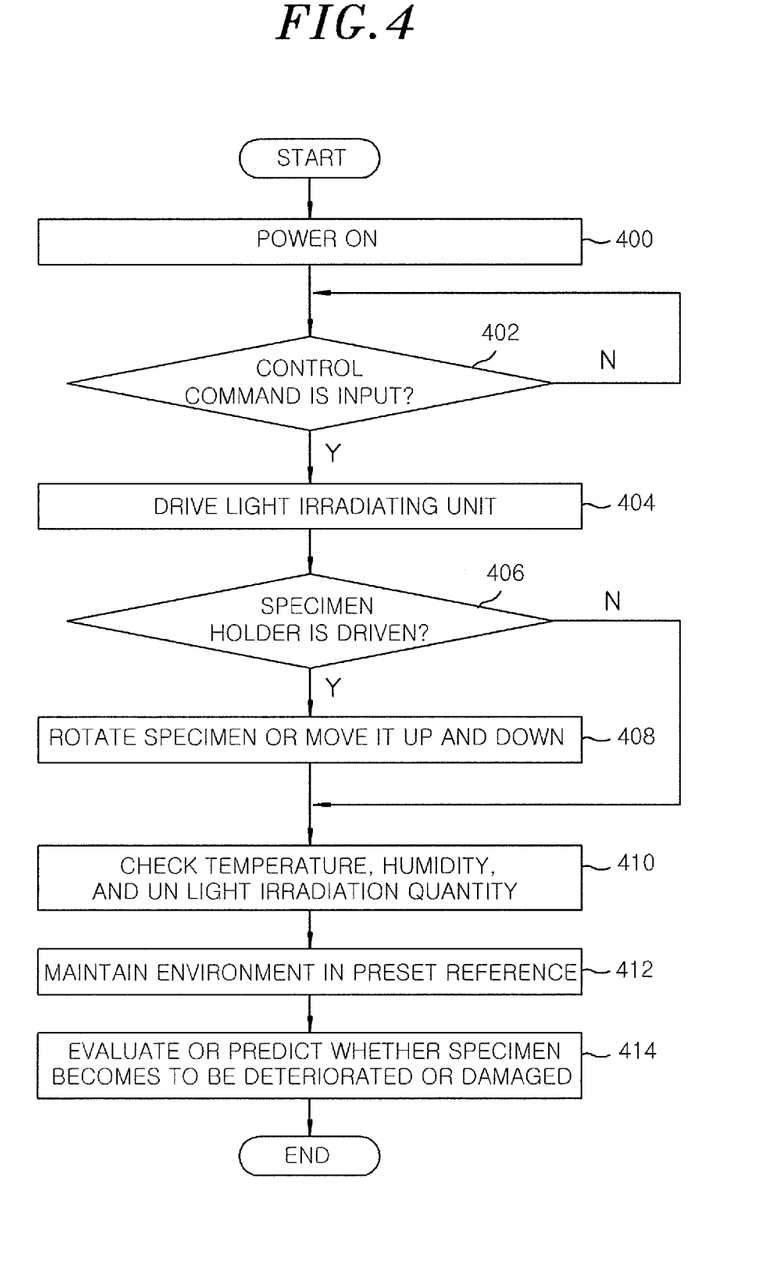
FIG. 4 is a flow chart illustrating an operation of a test apparatus of a accelerated photo-degradation using an electrodeless plasma light source, according to an embodiment of the present invention.

FIG. 4 is a flow chart illustrating an operation of the test apparatus of the accelerated photo-degradation using the electrodeless plasma light source, according to an embodiment of the present invention.

Referring to FIG. 4, at block 400, when the switch of the power supply 302 within the test apparatus of the accelerated photo-degradation is ON, the power supply 302 becomes to supply power to the control unit 300 and each of the functional blocks to derive the test apparatus of the accelerated photo-degradation.

Next, at block 402, when the user interface 304 receives the control command from the user, the user interface 304 transmits the control command to the control unit 300, and the control unit 300 performs a test of the photo-degradation based on the received control command.

That is, at block 404, the control unit 300 controls the light irradiating unit 306 to be driven to irradiate the light from the electrodeless plasma light source 110, and at block 406, the control unit 300 determines whether the specimen holder driving unit 314 is required to be driven according to the received control command or a predetermined test scheme of the photo-degradation. In case where the control unit 300 determines that it is required to be driven, at block 408, the control unit 300 rotates the specimen holder driving unit 314 at a scheduled time unit, or moves the specimen holder driving unit 314 up and down.

Next, at block 410, the control unit 300 receives temperature, humidity, and UV light irradiation quantity from the air conditioning unit 308 and the UV light radiometer 312, and at block 412, the control unit 300 controls the air conditioning unit 308 and the light irradiating unit 306 to maintain a predetermined environment based on the received values, thereby performing the temperature control, the humidity control and the UV light irradiation quantity control, etc.

With this performance, at block 414, it is possible to check a change of the specimen caused by the photo-degradation, thereby evaluating or predicting whether the specimen becomes to be deteriorated or damaged.

Meanwhile, the electrodeless plasma lamp, which is abundant with visible light but is poor in a rate of infrared light, is a lamp having a high color rendition more than color rendering index of 94 and providing a color temperature more than 5,300K similar to the solar light. Also, the electrodeless plasma lamp employed in the embodiment is a lamp providing a characteristic that an intensity of the short-wavelength UV light region near 300 nm same as the solar light is the lowest and comes to be higher gradually to the direction of long-wavelength, and an intensity of the short-wavelength visible light region near 500 nm is the highest and comes to be sharply lower in the region more than about 600 nm, and an intensity of infrared light region more than about 750 nm is substantially lower than the intensity of the solar light or xenon-arc light source.

The test apparatus 100 of the accelerated photo-degradation having such an electrodeless plasma lamp as a light source may be used with a single lamp or with multiple lamps. In case of using alone, an optical convex lens or reflector capable of condensing UV light without a loss may be used.

Even in case of using multiple lamps, a convex lens or a reflector may be used for the light to be condensed into the intended portion of irradiation. However, in case of using multiple lamps, a method of condensing the light into the intended portion of irradiation only with a proper arrangement of the lamps without using a convex lens and a reflector may be taken.

In case where an electrodeless plasma light source with a small output less than 0.5 kW is used, the output of the light is relatively smaller than the output of the conventional lamp for testing photo-degradation. Thus, even though multiple lamps are used all together, it is difficult to obtain a high intensity of UV light irradiation per unit area. Therefore, in order to implement a highly-accelerated acceleration test apparatus capable of performing high intensity of UV light irradiation with a high accelerated characteristic using such an electrodeless plasma light source, it is necessary to use a method in parallel that condenses the light emitted from the lamp into a small area using a reflective tube, a reflective lampshade, a condensing lens, etc. When such a device of light condensing is used, the important is that the light condensed into the surface of the specimen must indicate a uniform intensity of irradiation.

Light condensing by a common lens type or reflective lampshade provides the condensed light to be condensed into a point or an arc. Thus, it is difficult to obtain a uniform intensity of irradiation. Especially, it is not desired to use a common convex lens, reflective lampshade or cylindrical tube with a structure of a curvature of circle or oval presenting such a light condensing. Therefore, in the condensing device for the electrodeless plasma lamp, for example, a method condensing light uniformly through a light pipe 160 with a shape of square pipe or a light-transmitting rod 162 with a shape of square rod as shown in FIGS. 1 and 2 may be preferred.

Figure 2:
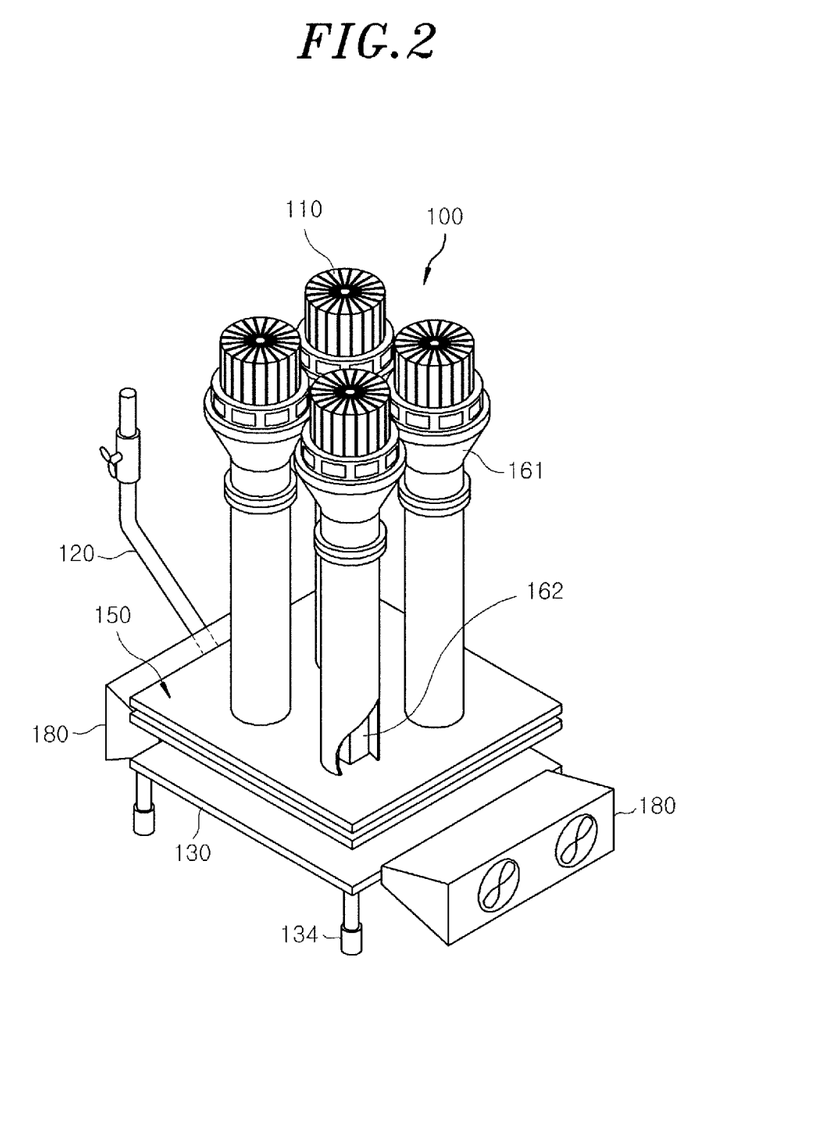

Here, the light pipe 160 with a shape of square pipe of FIG. 1 or the light-transmitting rod 162 with a shape of square rod of FIG. 2 is preferably to have a transmitting cross section of square so as for the light to be irradiated with a shape of square. An irradiating area per light source is desired to be adjusted in the range from 400 $mm^2$ to 40,000 $mm^2$. Light condensing for the irradiating area less than 400 $mm^2$ makes a difficulty to maintain an intensity of irradiation with reproducibility, and further as a temperature control for the surface of the specimen is relatively difficult due to a localized heat collection effect for the small area, it is difficult to ensure the reproducibility for the photo-degradation.

On the contrary to this, light condensing for the irradiating area more than 40,000 $mm^2$ may provide a low intensity of UV light irradiation to such an extent as to little meaning as light condensing for the accelerated acceleration test and thus is not desired to use. The most preferable irradiating area is in the range from 650 $mm^2$ to 10,000 $mm^2$.

The length of the light pipe and the light-transmitting rod is preferably to have a length of at least one times up to maximum ten times based on one actual length of the square cross section of light-transmitting. In case of shorter than the one times, a uniformity of the intensity of irradiance over the total irradiating area becomes to be poor, and in case of longer than the ten times, the whole intensity of irradiance is weakened.

The inner surface of the light pipe must be made of materials having a reflectivity of at least 90%. Preferred examples for such materials may be aluminum plate or film, fluorinated polymer such as polytetrafluoroethylene, or barium sulfate coatings which has a function of regular reflection or diffused reflection. In some cases, a quartz glass plate treated by a UV light reflective coatings may be used. The UV light reflective coating must have a reflectivity of at least 90% for the UV light with a wavelength of about 300-500 nm and the short-wavelength visible light, and must preferably have a reflectivity less than about 30% (i.e., transmitting more than about 70%) for the visible light with a long-wavelength more than about 600 nm and infrared light.

For the both end surfaces of the light pipe, a quartz glass lens with an excellent transmittance of UV light or a quartz glass plate with a certain thickness may be used. For the quartz glass plate, a plate provided with a filtering function capable of filtering UV light of a certain region may be used. In addition, it is desired to use anti-fogging coating or water repellent coating on the surface of the plate positioning in the direction of irradiating to the specimen in order to avoid a distortion of travels of light caused by fine water particles or droplets to be applied to the specimen.

Also, in order to increase the effect of removing infrared light, a method may be used in a way that both end surfaces of the light pipe is sealed with the sealed quartz glass plate, and a fluid with an excellent UV light transmittance or a distilled water is filled in the inside of the sealing, and a temperature of the fluid is controlled by a circulation-type cooling unit.

Here, a method may be taken in a way that the light emitting from the electrodeless plasma lamp is condensed using a common circular convex lens or reflecting shade, and then the condensed light is used. In this case, the light condensed by one or several convex lenses or a circular reflecting shade may be used together with the convex lens.

It is desired that the condensed light passes through a course of equalization for dispersing the light to be condensed into the focus while passing the previously mentioned light pipe or light-transmitting rod. For the dispersing course, a method of using a dispersing filter inducing scattering or of using a reflecting mirror with a function of scattering/reflecting within inside of the light pipe, or the like may be used.

In addition of the method using the light pipe or the light-transmitting rod for transmitting the light condensed into the focus to the surface of the specimen by a convex lens or a reflective shade at the focus, a method of using a light guide filled with a light fiber of quartz glass material or liquid compound allowing UV light to be transmitted may be used. As the light guide is advantageously capable of deforming or bending light into the curve within a certain allowable range contrary to the light pipe or the light-transmitting rod, it may present a favorable condition in manufacturing the apparatus upon setting a location between the lamp and the specimen.

Meanwhile, a temperature control for the irradiating area of the specimen may be possible by a control method of a conventional black panel temperature (BPT). In consideration that a UV light with much higher level of intensity of irradiation than that of the solar light is used, however, it may be desired to directly measure the surface of the specimen to be irradiated to control the temperature of the specimen, or to control the temperature based on a chamber temperature (CHT) regardless of the temperature of the specimen.

Here, a temperature control range of the surface of the specimen is ranged from the room temperature to 110° C., but a more preferred temperature control range is 30-85° C. The surface temperature of the specimen may vary, because the specimen accumulates, conducts and radiates a heat depending on the material and the color of the specimen under the same conditions of chamber temperature and lamp intensity of irradiation. Thus, the black panel temperature to be controlled in the acceleration test apparatus of the highly-accelerated photo-degradation may be different from the temperature of the black panel temperature to be obtained by the actual solar light.

The reason why the temperatures are different each other is that the surface temperature of the specimen to be obtained upon being irradiated with a light having a significantly lower rate of infrared light as the embodiment and the surface temperature of the specimen to be obtained upon being irradiated with the solar light having the same level of intensity based on UV light intensity of irradiation become to be different each other.

From the above reason, a temperature control of the surface of the specimen given for the test of super-acceleration photo-degradation may be more accurate to be adjusted with a direct measurement of the surface temperature of the specimen, compared to a temperature control to be adjusted with a thermometer of the black panel to be assembled as a part of the test apparatus regardless of the actual surface temperature of the specimen.

Here, a temperature sensor measuring the surface temperature of the specimen is preferably a wire cable type sensor coated by fluorine-resin cable of T-type. However, a temperature measurement of the surface of the specimen of the present invention is not limited to the above mentioned T-type and wire cable type sensor, and in addition to the such the contact-type thermometers, noncontact-type infrared thermometer also may be used.

Also, the temperature of the surface of the specimen and the temperature of the chamber of the present invention may be controlled under the condition of natural convection or by a forced air blowing and water spraying. The most preferred method is a forced blowing which takes place by controlling the amount of air to be blown to the surface of the specimen by a blowing fan 180 as shown in FIG. 2. Such the method which may be applied when the surface temperature of the specimen is higher than the chamber is applicable to the most cases.

When the intensity UV light irradiation maintains highly, or the photo-degradation of the heat-sensitive material is progressed, it may be insufficient to cool the surface of the specimen to a desired temperature only with a function of air blowing. In this case, in addition to the function of blowing by means of an air circulating within the chamber, it is desired to provide a more efficient cooling by blowing the air which is inhaled from the outside of the chamber and then is cooled by a chiller or a heat exchanger at the air conditioning unit 308 of FIG. 3. In case of using the chiller, it is desired to utilize a part of the cooled air and the air used for cooling the surface of the specimen together with the circulated cooling air to prevent the lamp from overheating.

In addition, in order to simulate the effects of the degradation by moisture during the irradiation of photo-degradation, a method of controlling the humidity within the chamber by means of the air conditioning unit 308 of FIG. 3 or of water spraying by means of the water spray nozzle 120 may be used.

In an embodiment of the present invention, in addition to the function of the humidity control and the water spraying, a method of applying ultrasonic waves to the specimen immersed into the ultrasonic water tank with the controlled temperature via the immersing unit 310 of FIG. 3 may be used. This method is effective in increasing a speed of penetration of moisture into the inside of the plastic or the film and also in quickly removing the additive near the surface. By this way, the effects of moisture infringement to the polymeric material due to the exposing to the outdoor precipitation and due condensation for a long-term period may be reproduced in the acceleration test apparatus of the (accelerated) photo-degradation in a short-term period.

While the specimen is immersed in the ultrasonic water tank, UV light irradiation is impossible from the view of structural aspect. Therefore, it is desired to carry out a cycle test so as for the test of the light irradiation and the test of the immersing into the ultrasonic water tank to be repeated alternatively with an automatic or manual way for a pre-set period. Accordingly, in the present invention, it is possible to use the ultrasonic water tank installed in the irradiation system of the photo-degradation, or to use the ultrasonic water tank to be provided as independent equipment.

The temperature of the water in the ultrasonic water tank is preferred in a range of 4° C.-90° C. In a lower temperature than this range of temperature, a portion of the water may freezes, and in a higher temperature than this range of temperature, excessive air bubbles may occur in the surface of the specimen, which may make a difficulty to carry out a test with reproducibility and also may induce a heat-sensitive material to be progressive thermal degradation.

The specimen of FIGS. 1 and 2 is fixed to the specimen holder 130. In the fixed state, the test may be carried out with the movable type (FIG. 1) or the fixed type (FIG. 2) at the position of light irradiation aligned to the fixed lamp and the condensing unit. In case of a test with one lamp only, it is desired to carry out a test with the fixed type, and in case of a test with the multiple lamps, in consideration that a deviation of intensity of UV light irradiation in each lamp may occur, it is desired to carry out a test with a rotating type in order to average out the deviation.

For a desirable rotating method of the specimen holder, the multiple lamps are arranged in a circle as shown in FIG. 1 so as for the light to be irradiated to the inner surface of the circle, and the inner surfaces of the circle to be irradiated are arranged to abut vertically each other so as to be formed in a rectangular shape to several tens of rectangular shapes, and thus specimen holders 130 corresponding to the rectangular shape to several tens of rectangular shapes are forced to rotate. If the specimen holder consisted of one band of the rectangular shape or the several tens of rectangular shapes is to say as one layer, it is possible to configure for the lamps, condensing units and specimen holders to be arranged in a plurality of layers.

Therefore, in the movable type holder with rotating, at least 4 specimens are possible to test at the same time, but it is more preferable to use a rotating holder capable of testing specimens in a range of 6-36 at the same time. The specimen holder with a specimen is of structure easy to move from the position of light irradiation into the ultrasonic water tank.

In case where it is designed that the ultrasonic water tank is located at the bottom of the apparatus and the UV light irradiating unit is located at the top of the apparatus, it may be possible to use an automatic device which moves the whole of the specimen holder from the position of light irradiation to the ultrasonic water tank with a vertical moving way. In case of manual moving, it is desired to mount the handle 132 which helps for easily removing the whole of the specimen holder from the apparatus and placing it to the ultrasonic water tank.

After progressing the light irradiation using the light irradiating unit 306 of the test apparatus 100 of the accelerated photo-degradation, the measurement of the photo-degradation of the surface of the plastic material may be performed in a mode that color difference ($\Delta E$) or yellowing index change ($\Delta YI$) is applied with specular component included or excluded by means of ASTM E313 standard using a color difference meter.

Hereinafter, embodiments with a variety of ways using the test apparatus 100 of the accelerated the photo-degradation and embodiments using a prior art are described comparatively.

First Embodiment

An intensity of irradiation was controlled to emit an intensity of UV light irradiance with about 600 W/m$^2$ (based on the intensity of UV light irradiance of about 300-400 nm) using the test apparatus 100 of the accelerated photo-degradation of FIG. 1. A specimen injected from the polypropylene resin (the black, Chronicles M1452U) for injection application was immersed in the water tank with a temperature of 40° C. with an ultrasonic vibration for one hour and without an ultrasonic vibration for one hour by a repetition period for two weeks. Next, while spraying water for 20 minutes every two hours under the condition of a chamber temperature of 15° C. and a humidity of 50% RH, variation of the color difference of the surface was measured from the testing until the cumulative UV light quantity reached to 100 MJ, 300 MJ and 500 MJ. The test results were shown that chrominance at 100 MJ was 0, at 300 MJ was 0 and at 500 MJ was 3 respectively.

As a comparative test (comparative example 1) in order to compare with the above test, the specimen of polypropylene resin as used in the first embodiment was treated using a xenon-arc photo-degradation tester based on the test condition pursuant to SAE J1960 standard, i.e., black panel temperature of 70° C., humidity of 50% RH, light irradiation for two hours and water spraying for one hour without the light irradiation. Next, variation of the color difference of the surface was measured from the testing until the cumulative UV light quantity reached to 100 MJ, 300 MJ and 500 MJ. The test results were shown that chrominance at 100 MJ was 0, at 300 MJ was 0 and at 500 MJ was 0 respectively.

As a second comparative test (comparative example 2), the specimen of polypropylene resin as used in the first embodiment was placed on the exposing test tool fixed at south-facing 37° located at Seosan city, Chungcheongnam-do, Korea of Korea Conformity Laboratories and was performed outdoor exposing test for 23 months from October, 2007 to September, 2009. Measured variation value of color difference using the accumulative UV light quantity during the test period was shown that chrominance at 100 MJ was 0, at 300 MJ was 1 and at 500 MJ was 3 respectively.

Second Embodiment

An intensity of irradiation of the light irradiating unit consisting of the electrodeless plasma lamp and the rod shape equalized condensing unit was adjusted to emit an intensity of UV light irradiance→irradiance with 1,200 W/m$^2$ using the test apparatus 100 of the accelerated photo-degradation of FIG. 2. Next, A specimen injected from the polyoxymethylene resin (the white, KEP F20-03) for injection application was tested under the condition of the chamber air temperature of 20° C. and of the humidity of 50% RH until the cumulative UV light quantity reached to 100 MJ, 300 MJ and 500 MJ, and the variation of color difference of the surface was measured. The test results were shown that chrominance at 100 MJ was 0, at 300 MJ was 2 and at 500 MJ was 6 respectively.

As a comparative test (comparative example 3) in order to compare with the above test, an intensity of irradiation was adjusted to emit an intensity of UV light irradiance with 120 W/m$^2$ using a xenon-arc photo-degradation tester. Next, the specimen of polyoxymethylene resin as used in the second embodiment was tested under the condition of the black panel temperature of 70° C., humidity of 50% RH and light irradiation for 100 minutes without a water spraying and light irradiation for 20 minutes with a water spraying until the cumulative UV light quantity reached to 100 MJ, 300 MJ and 500 MJ, and a variation of color difference of the surface was measured. The test results were shown that chrominance at 100 MJ was 0, at 300 MJ was 1 and at 500 MJ was 5 respectively.

Third Embodiment

An intensity of irradiation was adjusted to emit an intensity of UV light irradiance with 600 W/m$^2$ using the test apparatus 100 of the accelerated photo-degradation of FIG. 1. A specimen injected from the polycarbonate resin (colorless transparency, Bayer AL2647) for injection application was water sprayed for 20 minutes every two hours under the condition of the chamber temperature of 40° C. and the humidity of 50% RH. Next, a variation of yellowing change index of the surface was tested and measured until the cumulative UV light quantity reached to 100 MJ, 300 MJ and 500 MJ. The test results were shown that yellowing change index was 6 at 100 MJ, 11 at 300 ML and 12 at 500 MJ respectively.

As a comparative test (comparative example 4) in order to compare with the above test, the specimen of polycarbonate resin as used in the third embodiment was treated using a xenon-arc photo-degradation tester based on the test condition pursuant to SAE J1960 standard, i.e., black panel temperature of 70° C., humidity of 50% RH, light irradiation for two hours and water spraying for one hour without the light irradiation. Next, a variation of yellowing change of index of the surface was tested and measured until the cumulative UV light quantity reached to 100 MJ, 300 MJ and 500 MJ. The test results were shown that yellowing change index was 5 at 100 MJ, 10 at 300 ML and 11 at 500 MJ respectively.

Fourth Embodiment

An intensity of irradiation was adjusted to emit an intensity of UV light irradiance with 900 W/m$^2$ using the light irradiating unit consisting of the electrodeless plasma lamp and the rod shape equalized condensing unit in the test apparatus 100 of the accelerated photo-degradation of FIG. 2. A specimen injected from the acrylic resin (colorless transparency, LG Chemical IH830) for injection application was water sprayed for 20 minutes every two hours under the condition of the chamber air temperature of 25° C. and the humidity of 50% RH. Next, a variation of yellowing change index of the surface was tested and measured until the cumulative UV light quantity reached to 100 MJ, 300 MJ and 500 MJ. The test results were shown that yellowing change index was 0 at 100 MJ, 1 at 300 ML and 2 at 500 MJ respectively.

As a comparative test (comparative example 5) in order to compare with the above test, an intensity of irradiation was adjusted to emit an intensity of UV light irradiance with 600 W/m² using a metal ring photo-degradation tester. The specimen of acrylic resin as used in the fourth embodiment was water sprayed for 20 minutes every two hours under the condition of the black panel temperature of 70° C. and the humidity of 50% RH. Next, a variation of yellowing change of index of the surface was tested and measured until the cumulative UV light quantity reached to 100 MJ, 300 MJ and 500 MJ. The test results were shown that yellowing change index was 3 at 100 MJ, 8 at 300 ML and 12 at 500 MJ respectively.

As another comparative test (comparative example 6) in order to compare with the above test, the specimen of acrylic resin as used in the fourth embodiment was treated using a xenon-arc photo-degradation tester based on the test condition pursuant to SAE J1960 standard, i.e., black panel temperature of 70 □, humidity of 50% RH, light irradiation for two hours and water spraying for one hour without the light irradiation. Next, a variation of yellowing change of index of the surface was tested and measured until the cumulative UV light quantity reached to 100 MJ, 300 MJ and 500 MJ. The test results were shown that yellowing change index was 0 at 100 MJ, 0 at 300 ML and 1 at 500 MJ respectively.

As the test results according to the aforementioned embodiments and examples, tests of embodiments compared to tests of examples are capable of carrying out an acceleration test which irradiates with high intensity the UV light having a similar characteristic as a distribution of UV light power of the solar light. Accordingly, the acceleration test of the highly-accelerated photo-degradation of which acceleration performance is increased 10 times or more than that of typical test condition to be carried out by most commonly used xenon-arc photo-degradation tester can be carried out without the side effects of overheating of the specimen.

More specifically, the test of the photo-degradation by the test apparatus using the xenon-arc light source of a comparative example 1 was required approximately 178 days (6 months), but the test of photo-degradation of the first embodiment could be carried out by approximately 12 days based on the same UV light irradiation quantity. In consideration that total test period including the ultrasonic vibration immersing condition introduced to improve a filed reproducibility was 26 days, the test of the first embodiment is estimated to have about 7 times more accelerated properties compared to the test period of 178 days of the test of comparative example 1. Also, the test of the first embodiment is estimated to have about 27 times more accelerated properties compared to the test period of 23 months carried out under the condition of outdoor exposing test of the comparative example 2.

In addition, the test results of the first embodiment shows closer color difference change of the surface to the test results of the outdoor exposing test by means of the natural solar light according to the comparative example 2 rather than the test results by means of the xenon-arc light source according to the comparative example 1. Therefore, the accelerated acceleration properties is significantly improved and also the field reproducibility more superior than the xenon-arc light source apparatus, of course, depending on the proper setting of test condition, is understood to be secured.

The test of the second embodiment could implement 10 times faster highly-accelerated test condition than the test implemented with the test condition from which could obtain the highest value of accelerated properties of acceleration with the photo-degradation tester using the xenon-arc light source of the comparative example 3. Thus, the result of the acceleration test shows that the test to be needed to be carried out for 60 days based on the same UV light irradiation quantity can be carried out for 6 days only.

In addition, in spite of the significantly shortened test period, the test results of the second embodiment shows a similar variation of color difference of the surface as the variation to be confirmed from the test results by the xenon-arc light source of the comparative example 3. Thus, the acceleration test of the UV photo-degradation by means of highly-accelerated test method and test apparatus of the present invention is understood to have a sufficient reproducibility for the photo-degradation of the given plastic material.

The test of the third embodiment shows the acceleration test results of the photo-degradation irradiated by the UV light having a high intensity equivalent to 10 times based on the intensity of UV light irradiation used most widely for the test apparatus of the photo-degradation using the xenon-arc light source of the comparative example 4. The acceleration test method and apparatus of the embodiment could carry out the test within 12 days based on the same UV light irradiation quantity with which the system of the xenon-arc light source was needed to carry out the test for 178 days. Thus, the acceleration test faster equivalent to approximately 15 times could be carried out.

Further, in spite of the dramatically shortened test period, the test results of the third embodiment shows a similar variation as the variation of yellowing change index of the surface to be confirmed from the test results by the xenon-arc light source of the comparative example 4. Thus, the acceleration test of the photo-degradation by the highly-accelerated test method and apparatus of the embodiment is understood to be utilized sufficiently for a simulating application of solar light-inducing degradation of the plastic material.

The test of the fourth embodiment shows the acceleration test results of the photo-degradation irradiated by a high intensity of UV light equivalent to 1.5 times and 15 times respectively based on the intensity of the UV light irradiation used most widely for the test system of the photo-degradation using the metal ring light source of the comparative example 5 and the xenon-arc light source of the comparative example 6.

The acceleration test method and apparatus of the present invention carried out the test of the photo-degradation in 8 days based on the same UV light irradiation quantity for which the system of metal ring light source as a system of the highly-accelerated photo-degradation was needed to be carried out the test for 12 days and the system of common xenon-arc light source was needed to be carried out the test for 178 days, thereby carrying out the acceleration test faster equivalent to 1.5 times and 22 times respectively.

In addition, it is understood that the test results of the photo-degradation by the metal ring light source of comparative example 5 and the test results of the photo-degradation by the xenon-arc light source are different each other in the variation of yellowing change index of the surface, and the method of acceleration test using the system of metal ring light source is possible for the highly-accelerated acceleration test, but the system of xenon-arc light source varies widely in reproducibility. However, the test results of the acceleration test method and apparatus of the present invention is able to derive a similar test result of photo-degradation as that of xenon-arc light source even with the highly-accelerated acceleration test.

As described in the above, according to the embodiments of the present invention, the acceleration test of the highly-accelerated photo-degradation irradiating a high intensity of UV light corresponding to 120-1,200 W/m² without a thermal damage in the surface of the specimen even without using an excessive cooling unit by means of the electrodeless plasma lamp having a similar UV light region as the solar light power spectrum can be implemented, and also can obtain the immersing effect within a short time at the ultrasonic vibration water tank implementing a short-term moisture infringement effect.

The aforementioned test apparatus of the highly-accelerated photo-degradation may be used for the test of photo-degradation (or weather proof) for all materials and products, and especially, is useful when a rapid preliminary survey test is necessary prior to the test of photo-degradation requiring a long-term period of test more than 30 days by means of the system of xenon-arc light source. When an intensity of UV light irradiation of the present invention is selected to an appropriate level to acquire better reproducibility in accordance with the characteristics of photo-degradation of materials and products to be tested, and an immersing condition of the ultrasonic vibration water tank and conditions of operation, humidity, water spraying, etc. of the air conditioning unit and the chamber for controlling a surface temperature of the specimen are optimized, it may be possible to obtain an acceleration test result of the photo-degradation with better reproducibility.

Figure 5:
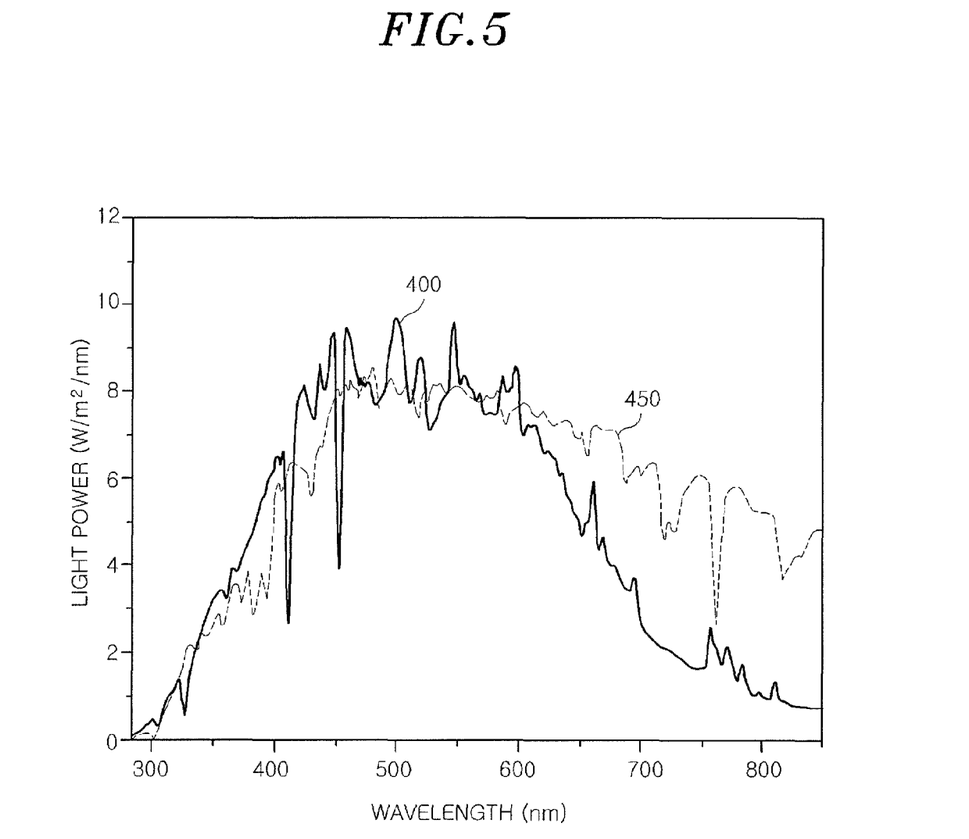
FIG. 5 is a graph illustrating a light power spectrum of the solar light compared to the electrodeless plasma lamp according to an embodiment of the present invention.

FIG. 5 is a graph illustrating a light power spectrum of the solar light compared to the electrodeless plasma lamp according to an embodiment of the present invention.

Referring to FIG. 5, reference numeral 400 is a light power spectrum of the electrodeless plasma lamp of the present invention and reference numeral 450 is a light power spectrum of the solar light which is amplified to a similar intensity of irradiation as the intensity of irradiation of the light power spectrum of the electrodeless plasma lamp.

As a result of comparison of the light power spectrum 400 of the electrodeless plasma lamp of the embodiment and the light power spectrum 450 of the solar light, it can be seen that two spectrums 400 and 450 have similar distributions each other in the UV light region below than 400 nm which is most important wavelength region for the photo-degradation of plastic materials or the like, and in the short-wavelength visible light region of about 400-500 nm.

Also, it can be seen that the light power spectrum 400 of the electrodeless plasma lamp comes to be rapidly lower compared to the light power spectrum 450 of the solar light from the visible light region of long-wavelength over 600 nm, and in the infrared light region over 800 nm, the difference between the two spectrums comes to be great. From such a difference, it can be seen that even though a high intensity of UV light irradiation is provided while the photo-degradation by the UV light maintains similar as that by the solar light, a heat collection effect by infrared light comes to be relatively smaller. Meanwhile, the electrodeless plasma lamp of the present invention contains short-wavelength UV light below 295 nm not included in the solar light less than the xenon-arc light source or the metal ring light source, and thus may provide an advantage of no need of a special filter for removing UV light in the test of photo-degradation which does not need a strict reproducibility of wavelength. Therefore, a cost of replacement of the filter which occupies a large proportion in the operation of common system of xenon-arc light source or metal ring light source is not necessary.

However, differently from the solar light power spectrum 250, the light power spectrum 200 of the electrodeless plasma lamp of the embodiment has a characteristic that light quantities near 327 nm, 412 nm and 453 nm are rapidly lowered. In case of the test where such a characteristic is of problem, it may be supplemented by a method using UV light-emitting diode (UV-LED) and visible light-emitting diode (VIS-LED) that shows a sharp emission peak at the region of about 325 nm and 410 nm. That is, the electrodeless plasma light source 110 may be mounted together with UV-LED and VIS-LED to the light irradiating unit of FIG. 1.

Further, in the embodiments of the present invention, an intensity of UV light irradiation condensing into the irradiating area may be adjusted in a range of 120 W/m²-1,200 W/m², depending on number of electrodeless plasma lamps, distance between the lamp and the specimen, size and length of the light pipe or light-transmitting rod, etc. Of course, the intensity of irradiation may be adjusted below 120 W/m². In this case, however, it is difficult to satisfy the required condition of the highly-accelerated acceleration test. Adversely, in case where the intensity of irradiation is adjusted over 1,200 W/m², it is difficult to suppress or control the excessive temperature rise caused by a heat collection effect generating from the light condensing.

As described in the above, the test apparatus and method of accelerated photo-degradation using an electrodeless plasma light source according to the embodiments of the present invention is used to predict and evaluate within a short-term period a photo-degradation characteristic caused by light such as UV light or visible light, etc. exposing to a polymeric material and an organic material, an organic-inorganic composite material or components and products containing these materials, and performs an evaluation or a test of degradation and damage caused by photo-degradation of the materials and products within a short-term period using the electrodeless plasma lamp as a light source of photo-degradation test, wherein the electrodeless plasma lamp is abundant with UV light and short-wavelength visible light, but substantially does not contain infrared light.

Although the present invention has been described in connection with specific embodiments, it will be appreciated that various modifications and alterations may be made without departing from the scope of the invention. Therefore, the scope of the present invention is not limited to the embodiments set forth herein, and shall be determined by the following claims and the equivalents.

The invention claimed is:

1. A test apparatus of accelerated photo-degradation measuring a degradation caused by photo-degradation in a material or a product by light containing UV light and visible light that simulate the solar light-inducing degradation, the apparatus comprising:
 a light irradiating unit configured to irradiate light using at least one electrodeless plasma lamp;
 a light condensing unit configured to collect light emitted from the light irradiating unit and irradiate the light uniformly into the surface of the specimen for the material or the product; and
 a specimen holder configured to fix the specimen, wherein the specimen holder being fixed at a predetermined position or rotated,
 wherein the at least one electrodeless plasma lamp generates light having a light power spectrum similar to a solar light in a region of UV light and short-wavelength visible light corresponding to a range of about 300-500 nm.

2. The test apparatus of claim 1, further comprising:
 a plurality of light pipes connected to a plurality of electrodeless plasma lamps and configured to irradiate the light to a specimen chamber where the specimen holder is located, wherein each light pipe being in a shape of pipe including a material having a reflectivity of the UV light more than about 90% to the inside of the pipe;

a specimen chamber partition wall including the specimen chamber, wherein each of the light pipes is inserted vertically into each side of the partition wall with a shape of polygon or circle, and the partition wall is arranged to irradiate light from the plurality of electrodeless plasma lamps to the side of the specimen holder;

a water spray nozzle configured to spray water to the specimen, wherein the water being sprayed from the exterior of the specimen holder; and an air conditioning unit configured to adjust temperature and humidity of the specimen chamber.

3. The test apparatus of claim 2, wherein the light pipe is finished with a quartz glass plate coated with an anti-fogging agent or a water-repellent coating on the cross section or both sides inserted into the specimen chamber.

4. The test apparatus of claim 1, further comprising an immersing unit configured to move or fall the specimen holder into a water tank filled with water and to immerse the specimen in the ultrasonic vibration water tank for a predetermined period.

5. A test apparatus of accelerated photo-degradation using an electrodeless plasma light source, the apparatus comprising:
   a user interface configured to receive a control command;
   a control unit configured to perform the test of accelerated photo-degradation based on the control command and to perform a measurement for an intensity of UV light irradiating to the surface of the specimen in a certain wavelength or a band of the wavelength range;
   a light irradiating unit configured to irradiate light containing UV light and visible light simulating the solar light-inducing degradation using at least one electrodeless plasma lamp under the control of the control unit; and
   a specimen holder configured to fix the specimen, wherein the specimen holder being fixed at a predetermined position or being rotated so as for the light to irradiate uniformly to the specimen under the control of the control unit,
   wherein the at least one electrodeless plasma lamp generates light having a light power spectrum similar to a solar light in a region of UV light and short-wavelength visible light corresponding to a range of about 300-500 nm.

6. The test apparatus of claim 5, wherein the light irradiating unit comprises light-transmitting rods connected to a plurality of electrodeless plasma lamps and configured to transit the light to the specimen chamber where the specimen holder is located, each of the light-transmitting rods having a shape of a light pipe or rod vertically inserted into each segment of a specimen chamber partition wall with a shape of polygon or circle.

7. The test apparatus of claim 5, wherein the control unit is configured to control an air conditioning unit adjusting temperature and humidity of the specimen chamber and to receive UV light irradiation quantity from a UV light radiometer measuring a UV light irradiation quantity periodically or continuously to control the light irradiating unit so as for a constant intensity UV irradiance to maintain.

8. The test apparatus of claim 5, further comprising an immersing unit configured to move or fall the specimen holder into a water tank filled with water and to immerse the specimen in the ultrasonic vibration water tank for a predetermined period under the control by the control unit.

9. A test method of accelerated light-inducing degradation using an electrodeless plasma light source, the method comprising:
   receiving, at a control unit of a test apparatus of accelerated light-inducing degradation, a control command from a user interface;
   irradiating, based on the control command, light containing UV light and visible light simulating the solar light-inducing degradation to a specimen using at least one electrodeless plasma lamp;
   fixing a specimen holder with a specimen at a predetermined position within a specimen chamber or rotating; and
   identifying temperature, humidity and UV light irradiation quantity of the specimen chamber and adjusting the identified to a preset reference,
   wherein the at least one electrodeless plasma lamp generates light having a light power spectrum similar to a solar light in a region of UV light and short-wavelength visible light corresponding to a range of about 300-500 nm.

10. The test method of claim 9, wherein said irradiating light to a specimen comprises collecting the light emitted from the at least one electrodeless plasma lamp at a light condensing unit and irradiating the collected light to the surface of the specimen.

11. The method of claim 1, wherein the at least one electrodeless plasma lamp has light power that comes to be higher gradually as wavelength becomes longer up to about 300 nm to 500 nm and that comes to be lower gradually as wavelength becomes in the region of about 600 nm to 750 nm to generate light having a light power spectrum similar to the solar light, and
   an intensity of infrared light region is lower than the intensity of the solar light or xenon-arc light source.

* * * * *